(12) United States Patent
St. Laurent

(10) Patent No.: US 9,278,082 B2
(45) Date of Patent: *Mar. 8, 2016

(54) METHOD FOR TREATING CONTACT DERMATITIS

(71) Applicant: Olatec Industries LLC, New York, NY (US)

(72) Inventor: Joseph P. St. Laurent, Lakeville, MA (US)

(73) Assignee: OLATEC INDUSTRIES LLC, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/796,809

(22) Filed: Jul. 10, 2015

(65) Prior Publication Data

US 2016/0008314 A1 Jan. 14, 2016

Related U.S. Application Data

(63) Continuation of application No. 14/552,366, filed on Nov. 24, 2014, now Pat. No. 9,078,869, which is a continuation of application No. PCT/US2013/043921, filed on Jun. 3, 2013.

(60) Provisional application No. 61/655,936, filed on Jun. 5, 2012.

(51) Int. Cl.
*A61K 31/275* (2006.01)
*A61K 9/06* (2006.01)

(52) U.S. Cl.
CPC .................................. *A61K 31/275* (2013.01)

(58) Field of Classification Search
CPC .... A61K 31/10; A61K 31/095; A61K 31/275
USPC ............................................................ 514/526
See application file for complete search history.

(56) References Cited

U.S. PATENT DOCUMENTS

| 4,424,167 | A | 1/1984 | Oeckl |
| 4,536,599 | A | 8/1985 | Masuko et al. |
| 5,175,192 | A | 12/1992 | Ulrich et al. |
| 7,419,958 | B2 | 9/2008 | Wilson et al. |
| 7,423,064 | B2 | 9/2008 | Torrence |
| 8,829,046 | B2 | 9/2014 | St. Laurent |
| 9,078,869 | B2 | 7/2015 | St. Laurent |
| 2010/0221336 | A1 | 9/2010 | Fink et al. |
| 2010/0240756 | A1 | 9/2010 | St. Laurent |
| 2012/0157524 | A1 | 6/2012 | St. Laurent |

OTHER PUBLICATIONS

International Search Report for Application No. PCT/US2013/043921, filed Jun. 3, 2013.
Hsi et al.: Syntheses of Some Analogs of Rorifone, Scientia Sinica, Dec. 1974, vol. XVII, No. 6, pp. 743-751.

*Primary Examiner* — Jennifer M Kim
(74) *Attorney, Agent, or Firm* — Perkins Coie LLP; Viola T. Kung

(57) ABSTRACT

The present invention is directed to a method for treating skin inflammatory diseases such as dermatitis, psoriasis, and acne, and rosacea, by administering 3-methanesulfonylpropionitrile or a pharmaceutically acceptable salt or solvate thereof to a subject in need thereof. The method alleviates the symptoms of the disease treated. The active compound can be administered by a systemic route or topical route. Topical administration is a preferred route of administration.

12 Claims, No Drawings

METHOD FOR TREATING CONTACT DERMATITIS

This application is a continuation of U.S. application Ser. No. 14/552,366, filed Nov. 24, 2014, now U.S. Pat. No. 9,078,869; which is a continuation of PCT/US2013/043921, filed Jun. 3, 2013; which claims the benefit of U.S. Provisional Application No. 61/655,936, filed Jun. 5, 2012. The contents of the above-identified applications are incorporated herein by reference in their entireties.

FIELD OF THE INVENTION

The present invention relates to using 3-methanesulfonylpropionitrile, or its pharmaceutically acceptable salts for treating inflammation or inflammatory-related disorders, particularly acne, psoriasis, dermatitis, and rosacea.

BACKGROUND OF THE INVENTION

Inflammation is a process by which microbes or tissue injury induce the release of cytokines and chemokines from various cell types producing increased blood vessel permeability, upregulation of endothelial receptors, and thus increased egress of various cells of the innate and adaptive immune system which enter surrounding tissue and grossly produce the classical picture of inflammation, i.e. redness, swelling, heat and pain.

Inflammation is a localized reaction of live tissue due to an injury, which may be caused by various endogenous and exogenous factors. The exogenous factors include physical, chemical, and biological factors. The endogenous factors include inflammatory mediators, antigens, and antibodies. Endogenous factors often develop under the influence of an exogenous damage. An inflammatory reaction is often followed by an altered structure and penetrability of the cellular membrane. Endogenous factors, namely, mediators, antigens, and autogens define the nature and type of an inflammatory reaction, especially its course in the zone of injury. In the case where tissue damage is limited to the creation of mediators, an acute form of inflammation develops. If immunologic reactions are also involved in the process, through the interaction of antigens, antibodies, and autoantigens, a long-term inflammatory process will develop. Various exogenous agents, for example, infection, injury, radiation, also provide the course of inflammatory process on a molecular level by damaging cellular membranes which initiate biochemical reactions.

Current therapy is directed to some or all of the pathogenetic components of inflammation. For example, corticosteroids have a broad spectrum of activities and NSAIDS are more specifically anti-prostaglandin and analgesic. All current therapies have relatively high rates of adverse effects and adverse effects are severe and serious.

There is a need for a composition and a method for treating skin inflammatory diseases. The composition should be economic and easy to manufacture, and the method should be effective and have no significant side effects.

SUMMARY OF THE INVENTION

The present invention is directed to a method of treating an inflammatory skin disease or disorder, comprising the step of administering 3-methanesulfonylpropionitrile or a pharmaceutically acceptable salt thereof to a subject in need thereof, wherein the inflammatory skin disease or disorder is dermatitis, psoriasis, acne, or rosacea.

In one embodiment, the method treats atopic dermatitis and alleviates one or more symptoms selected from the group consisting of erythema, induration, lichenification, scaling, and oozing and crusting.

In one embodiment, the method treats psoriasis and alleviates erythema, scaling, and/or thickness of the psoriasis lesions.

In one embodiment, the method treats acne and alleviates acne lesions selected from the groups consisting of closed comedones, papules, pustules, nodules, and cysts.

In one embodiment, the method treats rosacea and alleviates one or more symptoms selected from the group consisting of erythema, telangiectasia, red domed papules and pustules, red gritty eyes, and burning and stinging sensations.

The active compound can be administered by local or systemic administration. Preferred route administration is topical administration or oral administration.

DETAILED DESCRIPTION OF THE INVENTION

Definition

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

"Solvates," as used herein, are addition complexes in which the compound is combined with an acceptable co-solvent in some fixed proportion. Co-solvents include, but are not limited to, ethyl acetate, lauryl lactate, myristyl lactate, cetyl lactate, isopropyl myristate, methanol, ethanol, 1-propanol, isopropanol, 1-butanol, isobutanol, tert-butanol, acetone, methyl ethyl ketone, acetonitrile, benzene, toulene, xylene(s), ethylene glycol, dichloromethane, 1,2-dichloroethane, N-methylformamide, N,N-dimethylformamide, N-methylacetamide, pyridine, dioxane, and diethyl ether.

"An effective amount," as used herein, is the amount effective to treat a disease by ameliorating the pathological condition or reducing the symptoms of the disease.

Pharmaceutical Compositions

Purified compound of 3-methanesulfonylpropionitrile can be prepared according to US2012/0157524, which is incorporated herein by reference in its entirety.

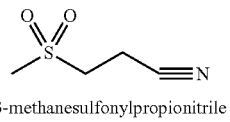
3-methanesulfonylpropionitrile 3-methanesulfonylpropionitrile

The present invention is directed to the use of a pharmaceutical compositions comprising one or more pharmaceutically acceptable carriers and 3-methanesulfonylpropionitrile, or a pharmaceutically acceptable salt, or solvate thereof. The active compound preferably has a purity of at least 85%, 90%, 95%, 97%, 98%, or 99%.

The active compound 3-methanesulfonylpropionitrile, or its pharmaceutically acceptable salt or solvate in the pharmaceutical compositions in general is in an amount of about 0.01-20%, or 0.05-20%, or 0.1-20%, or 0.2-15%, or 0.5-10%, or 1-5% (w/w) for a topical formulation; about 0.1-5% for an injectable formulation, 0.1-5% for a patch formulation, about 1-90% for a tablet formulation, and 1-100% for a capsule formulation.

In one embodiment, the active compound is incorporated into any acceptable carrier, including creams, gels, lotions or other types of suspensions that can stabilize the active compound and deliver it to the affected area by topical applications. In another embodiment, the pharmaceutical composition can be in the dosage forms such as tablets, capsules, granules, fine granules, powders, syrups, suppositories, injectable solutions, patches, or the like. The above pharmaceutical composition can be prepared by conventional methods.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and ploxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of 3-methanesulfonylpropionitrile may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but are not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone.

For example, a patch formulation of 3-methanesulfonylpropionitrile may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethylether.

Topical formulations including 3-methanesulfonylpropionitrile can be in a form of gel, cream, lotion, liquid, emulsion, ointment, spray, solution, suspension, and patches. The inactive ingredients in the topical formulations for example include, but not limited to, lauryl lactate (emollient/permeation enhancer), diethylene glycol monoethylether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

In one embodiment, lauryl lactate (for example, at about 0.1-10%, or about 0.2-5%, or about 0.5-5%) is included in the topical gel formulation. Lauryl lactate is considered safe for topical administration. Lauryl lactate is qualified for human use within pharmaceutical and cosmetic products. Lauryl lactate when used in a topical formulation enhances the permeability of the compound. Preferably lauryl lactate is purified to achieve >90%, preferably >95% purity; the high purity mitigates the presence of hydrolytic and oxidative agents. In addition, DMSO at 0.1-20%, or 0.5-10% (w/w) in the formulation provides suitable solubility of 3-methanesulfonylpropionitrile.

In another embodiment, diethylene glycol monoethylether is included in the topical gel formulation.

Method of Use

Inflammation is a process and a state of tissue pathology resulting from activation and continuation of activity of the innate and acquired components of the immune system. The arachidonic acid cascade and cytokine production and action in cell to cell interactions are critical components of immune activation and response, which lead to inflammation. Arachidonic acid resides in many cell membranes. When arachidonic acids are cleaved from the membranes, it can produce many of the known eicosinoids including prostaglandins and leukotrienes, which are known pro-inflammatory entities.

Applicant has discovered that 3-methanesulfonylpropionitrile inhibited pro-inflammatory cytokine release (e.g., IL-1β, IL-6, TNFα, IL-4 and IFNγ) from human peripheral blood mononuclear cells in vitro. Applicant has discovered that 3-methanesulfonylpropionitrile is anti-inflammatory when applied topically in the mouse ear swelling model, in which the inflammation was induced by arachidonic acid. Applicant has found that a gel formulation containing 3-methanesulfonylpropionitrile was well tolerated in 14-day dermal toxicity studies in rats and minipigs. The only effects seen after oral, systemic toxicity administration in rats and dogs were mild physiological effects including decreased body temperature, decreased respiratory rate, increased blood pressure and increased heart rate. The effects were seen at doses over 2000-fold above expected human therapeutic doses, which indicates that the compound would be well tolerated for systemic therapeutic use.

In a preferred embodiment, the present invention is useful in treating inflammation on the skin. The highly innervated skin has a high capacity for redness, swelling, and heat. In a skin system, the degree of tissue damage is frequently magnified out of proportion to the resulting inflammatory response. In the skin for example, merely firm stroking will cause release of the cytokines, IL-1 and TNF.

The present invention provides a method for treating inflammatory skin diseases such as rosacea, dermatitis, psoriasis, and acne (Acne vulgaris). The method comprises the steps of identifying a subject in need thereof, and administering to the subject 3-methanesulfonylpropionitrile, in an amount effective to reduce or eliminate the symptoms of the disease. The method alleviates the symptoms and signs of rosacea, dermatitis, psoriasis, and acne.

Skin is highly reactive to environmental stimuli and the epidermal component of keratinocytes is a very rich source of both arachidonic acid and pro-inflammatory cytokines of IL-1 and TNF. The skin dendritic cells, Langerhans cells, recognize and process antigens for further immune response of various lymphocytes and all of these cells are primarily regulated by cytokines through their specific cell surface receptors.

Dermatitis (also called eczema) is generic inflammation of the skin. Specific types of dermatitis include atopic, contact, nummular, and photo-induced.

Contact dermatitis is an inflammatory condition of the skin either of irritant exposure to the skin without specific adaptive immunologic pathogenesis or of allergic sensitization and subsequent exposure of the skin to the sensitizing allergen with specific adaptive immunologic pathogenesis. Both involve innate and acquired immune system response including arachidonic acid and cytokine components that initiate and propagate the disease through cell to cell messaging by eicosanoid and/or cytokine moieties produced by epidermal cells, macrophages, dendritic cells, neutrophils, eosinophils, and various T and B lymphocytes. Contact dermatitis may be either acute or chronic. The acute forms are pruritic with erythema, edema, and micro or macrovesiculation in the areas of skin contact by the initiating factor. The chronic forms are pruritic with milder erythema, scaling, lichenification, and possibly fissuring particularly on the hands.

Atopic dermatitis is a genetically determined disease that is part of the broader disease complex of atopy that includes asthma, hay fever, and atopic dermatitis. Many individuals with atopic dermatis have various mutations of the fillagrin gene that codes for an important epidermal structural protein that when defective, results in abnormal barrier function of the epidermis. The altered barrier allows exposure to multiple environmental allergens that are first recognized by innate immune responses involving arachidonic acid and eicosanoids and recruitment of eosinophils, mast cells, and other inflammatory cells that initiate an acute responses of itch, erythema, and subsequent scratching and additionally activate the adaptive immune responses that involve inflammation by lymphocytes predominantly of a TH 2 derivation and activity. Atopic dermatitis is responsive to a number of cytokine inhibitors such as cyclosporine, and tacrolimus.

Current theory of the pathogenesis of psoriasis is that in individuals who are genetically susceptible a triggering event in the epidermis such as injury or super antigen contact initiates an response of the innate immune system with arachidonic acid and eicosanoid generation, recruitment and activity of neutrophils. Subsequent transformation of the response to that of a TH 1 adaptive immunity with cytokine activation and activity of specific T lymphocytes effect the pathological changes in the epidermis and dermis, which result in the typical psoriasis lesions of plaques that are erythematous, thickened, and scaly. Psoriasis is responsive to various immunomodulators including cyclosporine, methotrexate, and a host of specific biologicals that interfere with cytokine signaling.

Acne vulgaris, a progressively inflammatory disorder of the pilosebaceous follicular unit especially of the face and upper chest and back is a very common disease of both males and females after initiation of puberty, and in females even prior to adrenal gland maturity. Increased production of androgenic hormones by adrenal, ovarian, and testicular glands and by the pilosebaceous unit itself produce an increase in sebum and changes in its lipid composition, which combine with follicular epithelial cells to produce some degree of obstruction of the infra-infundibular portion of the pilosebaceous follicle resulting in the initial lesion of acne, the microcomedo. This consequent dilation of the pore and the changed composition of sebum at puberty facilitate colonization of the follicle by *Propionibacterium acnes* bacilli that produce enzymes to degrade the triglycerides in sebum to free fatty acids that leak through the follicle into the dermis and incite arachidonic acid pathways of eicosanoid production and subsequent initiation of inflammation. The bacilli also initiate chemokine production that attracts further inflammatory cells to the area and consequent cytokine production and action to continue and amplify inflammation. Thus initiation and propagation of progressive inflammation in the microcomedo produces the evolution to the several hallmark lesions of inflammatory acne, papule, pustule, nodule, and cyst. The present invention is useful to treat common acne, comedonic acne, papulopustular acne, papulocomedonic acne, nodulocystic acne, acne conglobata, cheloid acne of the nape of the neck, recurrent miliary acne, necrotic acne, neonatal acne, occupational acne, acne rosacea, senile acne, solar acne or acne medicamentosa.

Rosacea is a chronic condition characterized by facial erythema and sometimes pimples. Rosacea typically begins as redness on the central face across the cheeks, nose, or forehead, but can also less commonly affect the neck, chest, ears, and scalp. In some cases, additional symptoms, such as semi-permanent redness, telangiectasia (dilation of superficial blood vessels on the face), red domed papules (small bumps) and pustules, red gritty eyes, burning and stinging sensations, and in some advanced cases, a red lobulated nose (rhinophyma), may develop. There are 3 subtypes of rosacea that affect the skin: erythematotelangiectatic rosacea, papulopustular rosacea, and phymatous rosacea.

3-methanesulfonylpropionitrile (MSPN), which is effective in inhibiting arachidonic acid induced inflammation and in inhibiting the release of pro-inflammatory cytokine, is effective to treat inflammatory skin diseases such as dermatitis, psoriasis, acne, and rosacea. MSPN is effective in treating atopic dermatitis and alleviating one or more symptoms selected from the group consisting of erythema, induration, lichenification, scaling, and oozing and crusting. MSPN is effective in treating psoriasis and alleviating erythema, scaling, and/or thickness of the psoriasis lesions. MSPN is effective in treating acne and alleviating acne lesions selected from the groups consisting of closed comedones, papules, pustules, nodules, and cysts.

MSPN is effective in treating rosacea and alleviating one or more symptoms selected from the group consisting of erythema, telangiectasia, red domed papules and pustules, red gritty eyes, and burning and stinging sensations.

The pharmaceutical composition of the present invention can be applied by local administration and systemic administration. Local administration includes topical administration. Systemic administration includes oral, parenteral (such as intravenous, intramuscular, subcutaneous or rectal), and other systemic routes of administration. In systemic administration, the active compound first reaches plasma and then distributes into target tissues. Topical administration and oral administration are preferred routes of administration for the present invention.

Dosing of the composition can vary based on the extent of the injury and each patient's individual response. For systemic administration, plasma concentrations of active compounds delivered can vary; but are generally $1\times10^{-10}$-$1\times10^{-4}$ moles/liter, and preferably $1\times10^{-8}$-$1\times10^{-5}$ moles/liter.

In one embodiment, the composition is applied topically onto the affected area and rubbed into it. The composition is topically applied at least one or two times a day, or 3 to 4 times per day, depending on the medical issue and the disease pathology being chronic or acute. In general, the topical composition comprises about 0.01-20%, or 0.05-20%, or 0.1-20%, or 0.2-15%, 0.5-10, or 1-5% (w/w) of the active compound. For example, the topical composition comprises about 1 or 5% (w/w) of the active compound. Depending on the size of the affected area, 0.2-85 mL, typically 0.2-10 mL, of the topical composition is applied to the individual per dose. The active compound passes through skin and is delivered to the site of discomfort.

In one embodiment, the pharmaceutical composition is administrated orally to the subject. The dosage for oral administration is generally 1-50, and preferably 1-10 mg/kg/day.

In one embodiment, the pharmaceutical composition is administrated subcutaneously to the subject. The dosage for subcutaneous administration is generally 0.3-20, and preferably 0.3-3 mg/kg/day.

Those of skill in the art will recognize that a wide variety of delivery mechanisms are also suitable for the present invention.

The present invention is useful in treating a mammal subject, such as humans, horses, and dogs. The present invention is particularly useful in treating humans.

The following examples further illustrate the present invention. These examples are intended merely to be illustrative of the present invention and are not to be construed as being limiting.

EXAMPLES

Example 1

Gel Formulation 1

Table 1 exemplifies one gel formulation containing 3-methanesulfonylpropionitrile.

TABLE 1

|  | 5% Gel | 1% Gel |
|---|---|---|
| 3-methanesulfonylpropionitrile | 5.0% | 1.0% |
| Dow Corning Elastomer Blend EL-8050ID | 61.0% | 69.0% |
| Labrafac Lipophile WL 1349 | 8.0% | 8.0% |
| Octisalate | 5.0% | 5.0% |
| Lauryl Lactate | 1.1% | 3.2% |
| Dimethyl Sulfoxide (DMSO) | 8.9% | 1.8% |
| Dow Corning 556 Cosmetic Grade Fluid | 7.0% | 7.9% |
| Squalene | 2.0% | 2.0% |
| Sunflower Seed Oil | 2.0% | 2.0% |
| Dow Corning Aerogel VM-2270 | 0.1% | 0.0% |
| Total | 100.0% | 100.0% |

Example 2

Gel Formulation 2

Table 2 exemplifies another gel formulation containing 3-methanesulfonylpropionitrile.

TABLE 2

|  | 1-5% Gel |
|---|---|
| 3-methanesulfonylpropionitrile | 1.0-5.0% |
| Diethylene Glycol Monoethylether | 5.0% |
| Acrylates/C10-30 alkyl acrylate crosspolymer (CARBOPOL ® Ultrez 20 polymer) | 0.50% |
| Trolamine (tris(2-hydroxyethyl)amine) | 0.47% |
| Purified Water | 89.03-93.03% |
| Total | 100.0% |

Example 3

Inhibition of Cytokine Activities 3-methanesulfonylpropionitrile (MSPN) was tested for its effects on in vitro cytokine release from human peripheral blood mononuclear cells (PBMCs). Secretion of cytokines by PBMCs plays a significant role in the inflammatory response.

MSPN was added to cultures of fresh human PBMCs at 162 M (22 µg/mL) in duplicate. One hour later, PBMCs were stimulated to secrete cytokines using the mitogens lipopolysaccharide and concanavalin A (ConA). Lipopolysaccharide at 50 pg/mL was used to stimulate the release of interleukin IL-1β, IL-6 and tumor necrosis factor TNFα. ConA at 20 g/mL was used to stimulate the release of IL-4 and ConA at 5 µg/mL was used to stimulate interferon IFNγ. The corticosteroid dexamethasone (100 nM) was used as a positive control. After 24 hours of incubation, the supernatants were assayed for the cytokines using the Luminex Bead kit. MSPN at 22 µg/mL inhibited the release of IL-1β, IL-6, TNFα, IL-4 and IFNγ by 95%, 98%, 98%, 7% and 21%, respectively. Dexamethasone inhibited the release of IL-1, IL-6, TNFα, IL-4 and IFNγ by 24%, 60%, 42%, 93% and 87%, respectively.

The results demonstrate that MSPN has a significant inhibitory effect on cytokines involved in the inflammatory process.

Example 4

Anti-Inflammatory Activity of 3-Methanesulfonylpropionitrile in Mice by Topical Application Purified 3-methanesulfonylpropionitrile was dissolved in vehicle (ethanol/acetone 1:1) to 5% (w/v). The active compound, indomethacin (positive control in vehicle), and vehicle were topically applied to mice and evaluated for anti-inflammatory activity in the topical arachidonic acid induced ear swelling model in mice, which is a model of irritant contact dermatitis.

Male ICR mice weighing 22±2 g were used and randomly divided; each group had 10 mice. Arachidonic Acid (0.5 mg in 20 µl of acetone:ethanol/1:1) was applied topically to the anterior and posterior surfaces of the right ear of each mice. Test substance and vehicle, as listed in Table 3 were similarly applied 30 min before and 15 min after arachidonic acid application. The thickness of the right ear and the left ear was measured and the difference calculated as an indication of the inflammation in the right ear. Ear swelling was measured by a Dyer model micrometer gauge at 60 and 90 minutes after arachidonic acid application as an index of inflammation. Percent inhibition was calculated according to the formula: Ic−It/Ic×100, where Ic and It refers to increase of ear thickness (mm) in control and treated mice, respectively. ANOVA and Dunnett's test were employed to ascertain significant difference between vehicle control and treated groups. Significance is set at P<0.05 level. The results measured at 90 minutes after arachidonic acid application are summarized in Table 3.

TABLE 3

| Test Substance | Conc mM (% w/v) | Dosage mg/20 μL | % Inhibition | P Value |
|---|---|---|---|---|
| Vehicle - acetone:ethanol (1:1) | NA | NA | NA | |
| Indomethacin (Positive control) | 14 (0.5) | 0.1 | 53 | <0.001 |
| 3-methanesulfonyl-propionitrile | 375 (5) | 1 | 36 | <0.001 |

3-methanesulfonyl-propionitrile resulted in a significant inhibition (36%) in the ear swelling induced by arachidonic acid, relative to that in the vehicle-treated group. The differences between MSPN-treated mice and vehicle-treated mice were determined to be statistically significant (p-value by t-test was <0.001).

Example 5

Systemic Administration of MSPN Formulation

This study was done to determine the systemic (plasma) exposure of MSPN after administration by the oral and subcutaneous routes to rats.

MSPN substance was prepared in water for oral administration and in saline for subcutaneous administration. Rats weighed 282 to 295 g were used in the study. Male rats (n=2) were given a single dose at 50, 160 or 500 mg/kg by both oral and subcutaneous routes. Female rats (n=2) were dosed only at 500 mg/kg by both oral and subcutaneous routes. The blood was drawn from each rat at 0.25, 1, 2, 3, 4, 6, 12, 24, and 48 hours and measured for MSPN concentration by LC/MS/MS.

For males, the average maximum plasma concentrations measured (Cmax) after oral dosing at 50, 160 or 500 mg/kg were 160, 560 and 12,000 μg/mL, respectively; and after subcutaneous dosing were 160, 760 and 3300 μg/mL, respectively. For females, the average Cmax after oral dosing of 500 mg/kg was 3800 μg/mL, and after subcutaneous dosing of 500 mg/kg was 9500 μg/mL. Half-lives were similar by both routes and for both sexes, and ranged from 8 to 15 hours.

The above results demonstrate that there was significant bioavailability of MSPN after both the oral and subcutaneous routes.

Example 6

Anti-Inflammatory Activity of 3-Methanesulfonylpropionitrile in Mice by Oral Application (Prophetic Example)

Purified 3-methanesulfonylpropionitrile is suspended in vehicle (1% Tween 80 in water) to 5-15 mg/mL. The test compound, dexamethasone (positive control in vehicle), and vehicle are orally administered to mice and evaluated for anti-inflammatory activity in the topical arachidonic acid induced ear swelling model in mice.

Male ICR derived mice weighing 22±2 g are used in this experiment. 10-15 mice are used for each group (active compound, positive control, and vehicle). All animals are maintained in a controlled temperature (22-24° C.) and humidity (60%-70%) environment with 12-hour light/dark cycles for at least one week prior to use.

Arachidonic acid (0.5 mg in 20 μL acetone) is applied topically onto the anterior and posterior surfaces of the right ear of test animals to induce inflammation. MSPN in vehicle (10 mL/kg) and vehicle (10 mL/kg, 50-150 mg/kg) are orally administered by gavage 1 hour before arachidonic acid, whereas dexamethasone is orally administered by gavage 3 hour before arachidonic acid challenge. At 60 minutes and 90 minutes after arachidonic acid induction of ear edema, the thickness of the right ear and the left ear is measured and the difference calculated as an indication of the inflammation in the right ear. Significant activity is defined as a statistically significant inhibition (p-value determined by t-test was <0.05) in arachidonic acid induced ear swelling relative to the vehicle-treated group.

Example 7

Treatment of Atopic Dermatitis (Prophetic Example)

Objectives:
To investigate the efficacy of the MSPN gel in patients having atopic dermatitis.

Formulation:
The gel formulation containing MSPN at 1-5% (Example 2) is used in this example. Placebo contains the same gel without the active compound.

Methodology:
This is a randomized, double-blind, placebo controlled, parallel treatment clinical activity study.

Male and female patients with mild to severe atopic dermatitis are enrolled after discontinuation of all treatments for atopic dermatitis for a period of 4 weeks before study initiation. Patients are randomized in a 1:1 ratio (active gel, placebo). A total of 300 patients are enrolled and treated.

The active Gel or placebo is applied twice a day to affected areas of the body for 12 weeks. The treatment results are evaluated at two week intervals until week 12 and then at 4 weeks after discontinuation of the study medication application.

Criteria for Evaluation:
Safety:
Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).

Efficacy:
Efficacy is evaluated utilizing:
1. an overall assessment of disease severity at study entry and at 2 week intervals until week 12 and subsequently at 4 weeks after study medication discontinuation. The investigator global assessment, IGA, is based upon a rating scale of 0 to 4 with 0=none or clear, 1=almost clear, 2=mild disease involvement, 3=moderate disease involvement, and 4=severe disease involvement, and:
2. separate evaluation of a representative target atopic dermatitis area of involvement for erythema, induration, lichenification, scaling, and oozing and crusting with each parameter rated on a 0-4 scale with 0=none or clear, 1=almost clear, 2=mild disease involvement, 3=moderate disease involvement, and 4=severe disease involvement.

Statistical analyses of each of these efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

Example 8

Treatment of Psoriasis (Prophetic Example)

Objectives:

To investigate the efficacy of the MSPN gel in patients having psoriasis vulgaris.

Formulation:

The gel formulation containing MSPN at 1-5% (Example 2) is used in this example. Placebo contains the same gel without the active compound.

Methodology:

This is a randomized, double-blind, placebo controlled, parallel treatment clinical activity study.

Male and female patients with mild to severe psoriasis vulgaris are enrolled. Patients discontinue all treatments for psoriasis for a period of 4 weeks before study initiation. Patients are randomized in a 1:1 ratio (active gel, placebo). A total of 200 patients are enrolled and treated.

The active Gel or placebo is applied twice a day to affected areas of the body for 12 weeks. The treatment results are evaluated at two week intervals until week 12 and then at 4 weeks after discontinuation of the study medication.

Criteria for Evaluation:

Safety:

Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).

Efficacy:

Efficacy is evaluated utilizing:

1. an overall assessment of disease severity at study entry and at 2 week intervals until week 12 and subsequently at 4 weeks after study medication discontinuation. The investigator global assessment, IGA, is based upon a rating scale of 0 to 4 with 0=none or clear, 1=almost clear, 2=mild disease involvement, 3=moderate disease involvement, and 4=severe disease involvement, and:

2. separate evaluation of a representative target psoriasis lesion for erythema, scaling, and thickness of each parameter rated on a 0-4 scale with 0=none or clear, 1=almost clear, 2=mild disease involvement, 3=moderate disease involvement, and 4=severe disease involvement.

Statistical analyses of each of the efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

Example 9

Treatment of Acne (Prophetic Example)

Objectives:

To investigate the efficacy of the MSPN gel in patients having acne vulgaris.

Formulation:

The gel formulation containing MSPN at 1-5% (Example 2) is used in this example. Placebo contains the same gel without the active compound.

Methodology:

This is a randomized, double-blind, placebo controlled, parallel treatment clinical activity study.

Male and female patients with mild to severe acne vulgaris are enrolled. Patients discontinue all treatments for acne for a period of 4 weeks before initiation of the study. Patients are randomized in a 1:1 ratio (active gel, placebo). A total of 500 patients are enrolled and treated.

The active Gel or placebo is applied to the affected area twice a day for 12 weeks. The treatment results are evaluated at two week intervals until week 12 and then at 4 weeks after discontinuation of the study medication.

Criteria for Evaluation:

Safety:

Safety is evaluated by general history and physical signs, laboratory testing for hematology, serum chemistry, and urinalysis, and by evaluations of local application site tolerability parameters of erythema, scaling, dryness, stinging/burning utilizing a rating scale of "0" (None) to "3" (Severe).

Efficacy:

Efficacy is evaluated utilizing:

1. an overall assessment of disease severity at study entry and at 2 week intervals until week 12 and subsequently at 4 weeks after discontinuation of the study medication. The investigator global assessment, IGA, is based upon a rating scale of 0 to 4 with 0=none or clear, 1=almost clear, 2=mild disease involvement, 3=moderate disease involvement, and 4=severe disease involvement, and:

2. separate counts of all types of acne lesions i.e. open and closed comedones, papules, pustules, nodules, and cysts.

Statistical analyses of each of the efficacy evaluations are performed for each of the 2 week study time points. Definitive evaluation of efficacy is based upon comparisons of active to vehicle groups at end of treatment at 12 weeks. The 4 week-post treatment evaluation is utilized to evaluate durability of treatment effect after medication discontinuation.

Example 10

Treating Rosacea

Patient A is 58-year old male with a long history of Rosacea. When Patient A experienced a flare-up, Patient A had redness on his nose, cheeks, chin, and forehead. Patient A also had get little bumps on the red parts of their faces. Patient A was provided with a gel formulation containing 5% of 3-methanesulfonylpropionitrile (see Example 2).

Following each flare-up, Patient A applied the 5% gel formulation on the red areas twice a day until the redness cleared, which took an average of 3 days.

Example 11

Treating Eczema on the Elbow

Patient B is a male at age 58, suffering from eczema (atopic dermatitis), which is a chronic skin problem that causes the skin on his elbows and knees to become dry, itchy and red—sometimes even cracked and leathery. Patient B was provided with a gel formulation containing 5% of 3-methanesulfonylpropionitrile (see Example 2).

Patient B applied 5% gel formulation once a day to the affected areas, rubbing it in well, until the symptoms resolves. The treatment period was typically 2-3 days and at most 5 days depending on the severity of the symptoms.

Example 12

Treating Acne Around the Shoulder Area of Back

Patient C is a 23-year old female. Patient C developed acne on her shoulder and back. Patient C was provided with a gel formulation containing 5% of 3-methanesulfonylpropionitrile (see Example 2).

Patient C applied the 5% gel formulation once a day and noticed improvement every day until her acne had cleared up. The treatment period was approximately 5 days.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method of treating an acute form of contact dermatitis, comprising the step of:
   administering to a subject in need thereof 3-methanesulfonylpropionitrile, in an amount effective to reduce or eliminate the symptoms of acute contact dermatitis.

2. The method according to claim 1, wherein said symptoms are selected from the group consisting of pruritic with erythema, edema, and microvesiculation or macrovesiculation in the areas of skin contact by an initiating factor.

3. The method according to claim 1, wherein said 3-methanesulfonylpropionitrile is administered by topical administration.

4. The method according to claim 3, wherein said 3-methanesulfonylpropionitrile is administered in a form of gel, cream, lotion, liquid, emulsion, ointment, spray, solution, suspension, and patches.

5. The method according to claim 1, wherein said 3-methanesulfonylpropionitrile is administered by oral administration.

6. The method according to claim 5, wherein said 3-methanesulfonylpropionitrile is administered in a form of tablets or capsules.

7. A method of treating a chronic form of contact dermatitis, comprising the step of:
   administering to a subject in need thereof 3-methanesulfonylpropionitrile, in an amount effective to reduce or eliminate the symptoms of chronic contact dermatitis.

8. The method according to claim 7, wherein said symptoms are selected from the group consisting of pruritic with mild erythema, scaling, lichenification, and fissuring.

9. The method according to claim 7, wherein said 3-methanesulfonylpropionitrile is administered by topical administration.

10. The method according to claim 9, wherein said 3-methanesulfonylpropionitrile is administered in a form of gel, cream, lotion, liquid, emulsion, ointment, spray, solution, suspension, and patches.

11. The method according to claim 7, wherein said 3-methanesulfonylpropionitrile is administered by oral administration.

12. The method according to claim 11, wherein said 3-methanesulfonylpropionitrile is administered in a form of tablets or capsules.

* * * * *